US00PP08508P

United States Patent [19]

Moore

[11] Patent Number: Plant 8,508

[45] Date of Patent: Dec. 21, 1993

[54] ORNAMENTAL DWARF NECTARINE—LEPRECHAUN CULTIVAR

[75] Inventor: James N. Moore, Fayetteville, Ark.

[73] Assignee: University of Arkansas, Fayetteville, Ark.

[21] Appl. No.: 954,021

[22] Filed: Sep. 30, 1992

[51] Int. Cl.[5] ..... A01H 5/00

[52] U.S. Cl. ..... Plt./41.4

[58] Field of Search ..... Plt./41.4

[56] References Cited

U.S. PATENT DOCUMENTS

P.P. 6,283 9/1988 Zaiger et al. ..... Plt. 41.4

OTHER PUBLICATIONS

Voss, Donald H., (1992) "Relating Colorimeter Measurement of Plant Color to *The Royal Horticultural Society Colour Chart*" Hortg. Science, vol. 27(12), pp. 1256–1260.

*Primary Examiner*—James R. Feyrer

[57] ABSTRACT

Description and specifications of a new and distinct ornamentla dwarf nectarine variety which originated from the $F_2$ population of a hand-pollinated cross of an unnamed dwarf nectarine selection (non-patented) and the Arkansas Peach Selection 164P (non-patented) are provided. This new ornamental dwarf nectarine variety can be distinguished by its dwarf plant size, bright green foliage, symmetrical plant shape, and attractive yellow/red glabrous fruit.

3 Drawing Sheets

SUMMARY OF THE INVENTION

The new and distinct variety or ornamental dwarf nectarine originated form a hand-pollinated $F_2$ cross of an unnamed dwarf nectarine selection (non-patented)-×Arkansas Peach Selection 164P (non-patented) made in 1980 at the Arkansas Agricultural Experiment Stations Fruit Substation at Clarksville, Ark. Neither of the parent trees has been released. The seeds resulting from this controlled hybridization were germinated in a greenhouse in the spring of 1981 and planted in a field on the Arkansas Agricultural Experiment Station in Clarksville, Ark. The seedlings fruited during the summer of 1983 and one, designated Ark. 327, was selected for its dwarf stature and attractive dense, green foliage.

During 1983, the original plant selection was propagated asexually at the above noted experimental station by budding onto standard peach rootstocks and a test plot of four plants was established. Subsequently, additional test plantings have been established with asexually multiplied plants at two additional locations in Arkansas.

The new variety has been asexually multiplied several times since 1983 by budding onto peach rootstocks and by rooting softwood cuttings. It roots well from softwood cuttings and no incompatibility with peach rootstocks has occurred following budding. During all asexual multiplication, the characteristics of the original plant have been maintained and no aberrant phenotypes have appeared.

Plants of the new variety exhibit the typical genetic dwarf growth habit. They produce dense, closed foliage canopy due to their much-branched shrub-type of growth. No central leader is formed and plants develop a vase shape with little pruning. Plants reach only about five feet in height in five years. Leaves are longer then those of standard peach trees.

Leaves of the new variety are an attractive bright green in color and are retained by the plant throughout the growing season. Flowers are pink in color and are present on the plant from March 19 to March 31 in central Arkansas. Fruits are small in size (ca. 59.5 g), round in shape, freestone, glabrous (nectarine), and attractive, having a yellow-orange ground color with red blush on surface. Fruit flesh is a uniform yellow-orange color with good firmness. Fruits have good, typically nectarine flavor. Ripening date averages July 15 in central Arkansas.

Trees have been hardy to −23° C. and show good resistance to bacterial spot, but fruits are susceptible to brown rot.

The distinctive features of the new variety are its much dwarfed growth habit, its attractive bright green leaves, and its dense, symmetrical plant form. Its primary value is use as an ornamental dwarf shrub with attractive foliage and edible nectarine fruits.

The new variety has been named the Leprechaun cultivar.

BRIEF DESCRIPTION OF THE PHOTOGRAPHS

The accompanying photographs show typical specimens of the plant in leaf, plant in bloom, and fruit of the new variety in color as nearly true as it is reasonably possible to make in a color illustration of this character.

DETAILED DESCRIPTION OF THE NEW VARIETY

The following is a detailed description of the botanical and pomological characteristics of the subject ornamental dwarf nectarine. Color data are readings from a Minolta Chroma Meter CR-200, version 3.0 which measures absolute chromaticity in tristimulus values X, Y, and Z as determined by the Commission Internationale de l'Eclairage. Color was determined using the CIE Yxy system. Calibration was performed using a standard white plate supplied by the manufacturer. These color data are supplemented with Royal Horticultural Society Colour Chart descriptions obtained by computer-matching of electronic readings to R.H.S. color references.

Where dimensions, sizes, colors, and other characteristics are given, it is to be understood that such characteristics are approximations of averages set forth as accurately as practicable.

The descriptions reported herein are from specimens grown at Clarksville, Ark.

Plant:

*Size.*—Dwarf. For trees 5 years of age: height=134.6 cm; width=170.2 cm.

*Form.*—Dense, much branched, shrub-type growth habit, with no central leader, with symmetrical form.

*Cold hardiness.*—Hardy to −23° C.

*Disease resistance.*—Resistant to bacterial leaf spot, susceptible to brown rot.

*Productivity.*—Very productive and consistent from year to year.

Foliage:

*Shoots.*—Mature shoot length 20.2 cm; diameter base 8.4 mm, midpoint 7.8 mm, terminal 7.2 mm. Mature shoot color: base Y=13.70, x=0.3811, y=0.3635, Brown (200D); midpoint Y=13.65, x=0.4012, y=0.3718, Grey-Brown (199A); terminal Y=13.75, x=0.4015, y=0.3784, Grey-Brown (199A); Young shoot color: base Y=20.19, x=0.3920, y=0.4197, Yellow-Green (146B); midpoint Y=29.75, x=0.3717, y=0.4308, Yellow-Green (146D); terminal Y=33.55, x=0.3693, y=0.4264, Yellow-Green (146D); Internode length: 6-10 mm, avg. 7.6 mm.

*Leaves.*—Mature leaf size: length 22.88 cm; diameter at widest point 3.14 cm. Mature leaf color: Abaxial base Y=10.95, x=0.3434, y=0.3989, Yellow-Green (147A); midpoint Y=10.76, x=0.3376, y=0.3934, Yellow-Green (147A); terminal Y=10.19, x=0.3341, y=0.4054, Yellow-Green (147A); Adaxial base Y=11.08, x=0.3456, y=0.4098, Yellow-Green (146A); midpoint Y=10.47, x=0.3401, y=0.4074, Green (137A); terminal Y=10.09, x=0.3377, y=0.4054, Green (137A). Petiole length; 15.6 mm. Leaf glands: reniform, 3-4 per leaf, avg. 3.4. Located on basal portion of leaf blade near juncture with petiole.

Bark:

*Color.*—New wood: Yellow-Green Group (146D); Mature wood: Grey-Brown Group (199A).

*Texture.*—Smooth

*Lenticels.*—Density: avg. 4.7 per $cm^2$; Shape: horizontal oblong; Size: horizontal, 1-2.5 mm, avg. 1.66 mm; vertical, 0.5-2 mm, avg. 1.1 mm.

Flowers:

*Date of bloom.*—First, March 19; 50%, March 23; Full, March 31.

*Diameter.*—32 mm.

*Color.*—Pink Red-Purple Group (68D).

*Petals per flower.*—5.

*Flowers per cluster.*—1.

*Pollen.*—Present and normal. Flowers are self fertile.

Fruit:

*Size.*—Small, avg. 59.54 g; diameter at equator 47.7 mm; length base to apex 49.0 mm.

*Shape.*—Round, symmetrical, with slight suture bulge.

*Skin.*—Glabrous; ground color Yellow-Orange (23A) with red blush (Red Group 46B) over 50% of surface. Skin medium thick and tenacious to flesh.

*Flesh.*—Uniform Yellow-Orange (20B) throughout; freestone; good firmness; no tendency to split; good eating quality. Flavor mild, subacid, with little aroma, fibers moderate but tender.

*Storability.*—Fruit stores well if harvested at firm-ripe stage of maturity a nd cooled immediately.

*Ripe date.*—July 15 in central Arkansas. Ripening of individual fruit is uniform and concentrated on tree.

*Soluble solids.*—13.5%

Seed:

*Size.*—Length 30.2 mm; width 26.1 mm.

*Shape.*—Slightly oblong, with deep furrowing and pitting.

*Color.*—Greyed-Orange Group (167C).

*Splitting.*—None observed.

Uses: Fresh consumption, canned, frozen.

The Variety

The most distinctive features of the variety are its dwarf growth habit, its attractive green foliage and its attractive yellow/red frutis.

I claim:

1. A new and distinct variety of ornamental dwarf nectarine, substantially as illustrated and described, characterized by its dwarf stature, bright green foliage, and attractive yellow-red fruits.

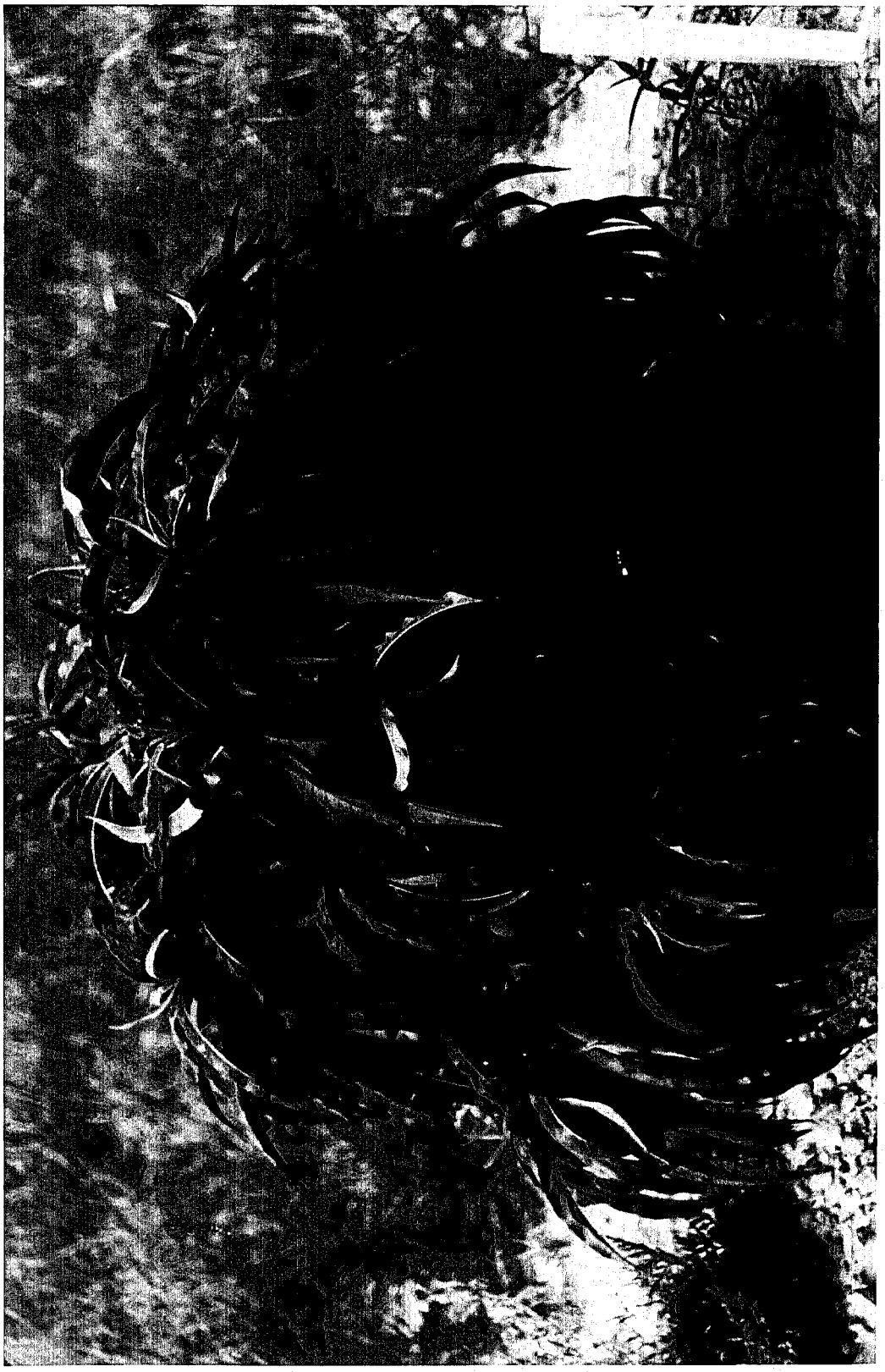

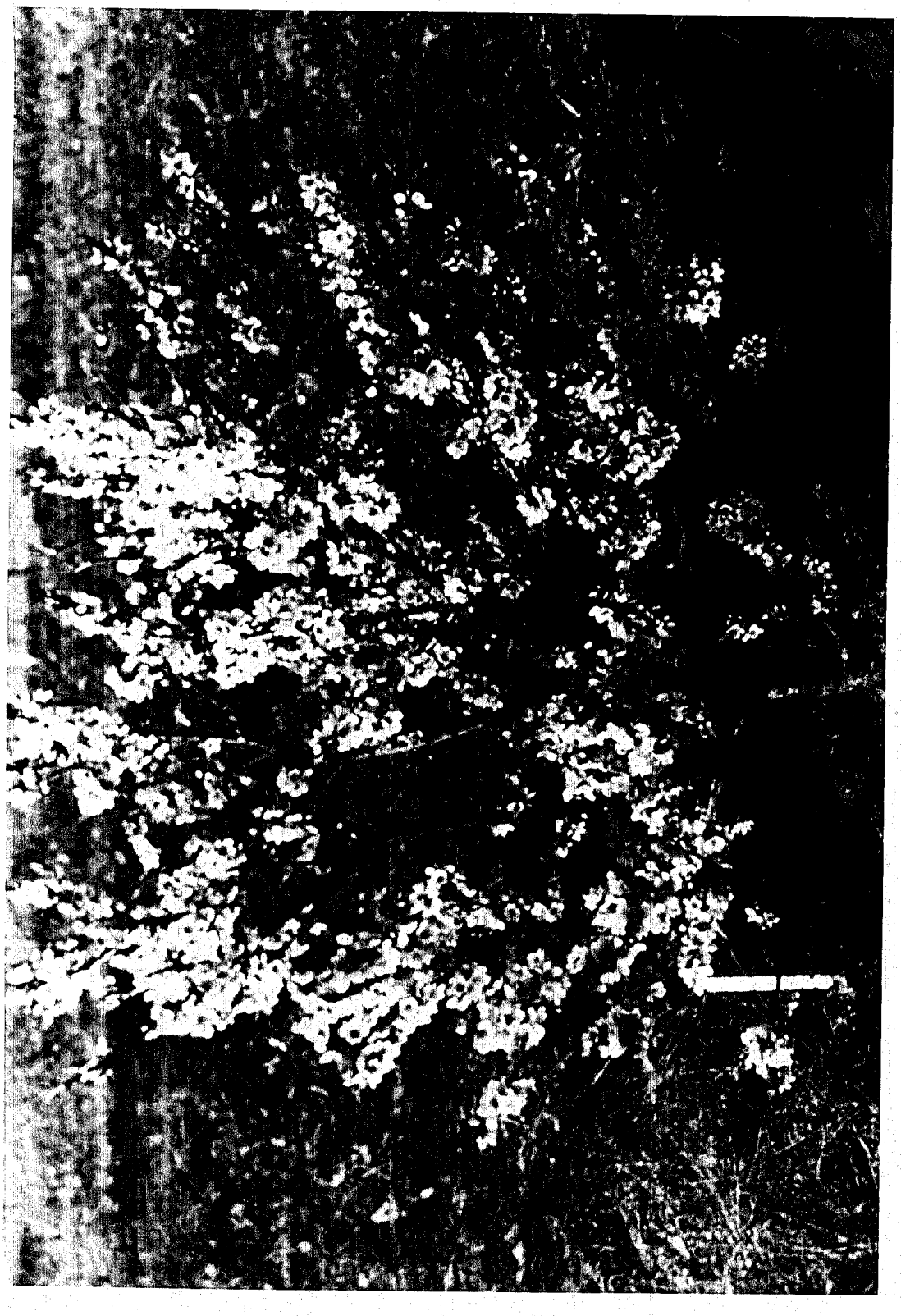

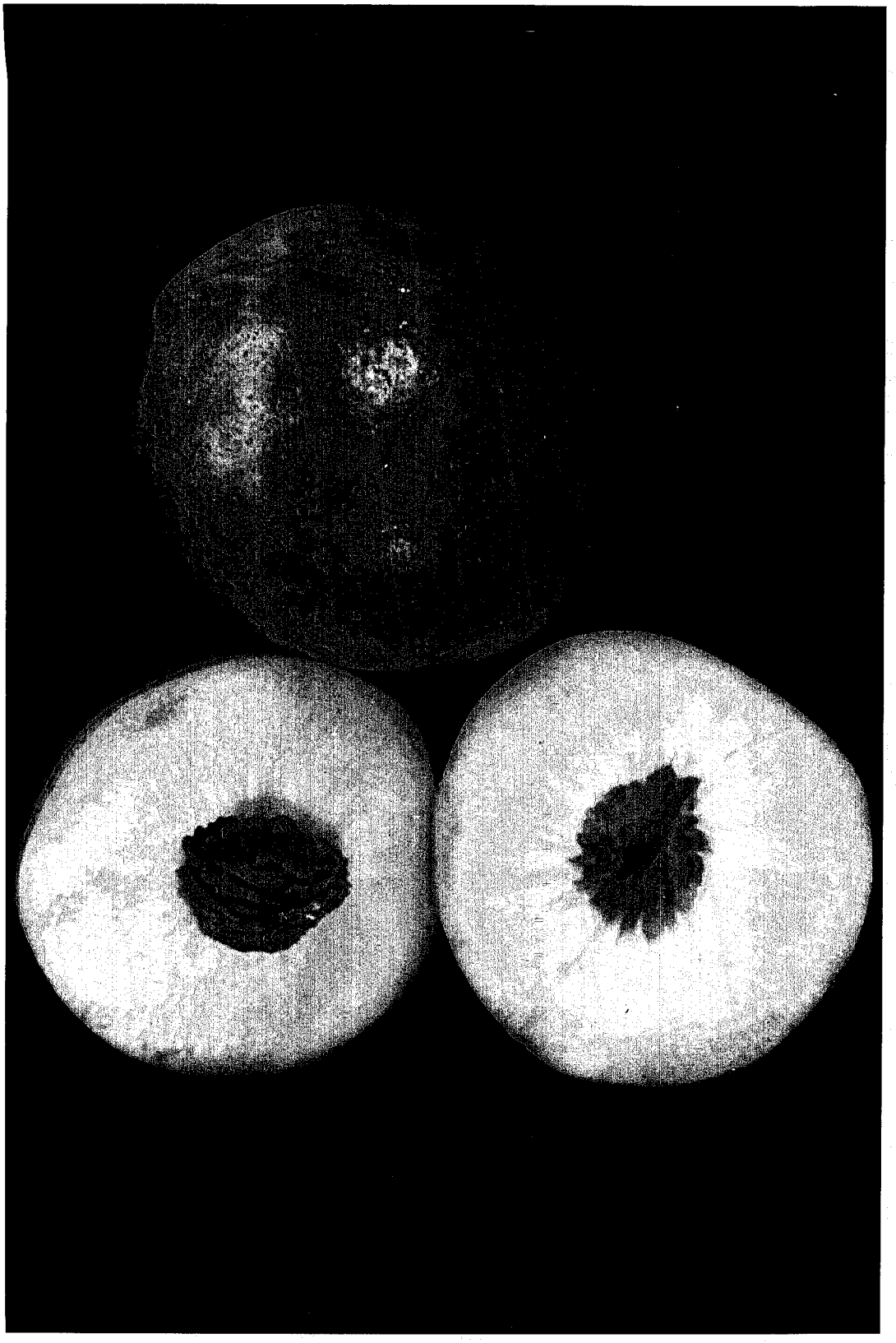

* * * * *